(12) United States Patent
Kirsch et al.

(10) Patent No.: US 10,045,107 B2
(45) Date of Patent: Aug. 7, 2018

(54) EARTIP THAT CONFORMS TO A USER'S EAR CANAL

(71) Applicant: HARMAN INTERNATIONAL INDUSTRIES, INC, Stamford, CT (US)

(72) Inventors: James M. Kirsch, Salt Lake City, UT (US); Branden Sheffield, Saratoga Springs, UT (US); Jason Walker, Saint Louis, MO (US)

(73) Assignee: HARMAN INTERNATIONAL INDUSTRIES, INCORPORATED, Stamford, CT (US)

( * ) Notice: Subject to any disclaimer, the term of this patent is extended or adjusted under 35 U.S.C. 154(b) by 0 days.

(21) Appl. No.: 14/805,365

(22) Filed: Jul. 21, 2015

(65) Prior Publication Data

US 2017/0026732 A1   Jan. 26, 2017

(51) Int. Cl.
*H04R 1/10* (2006.01)
*A61F 11/10* (2006.01)
*H04R 25/00* (2006.01)

(52) U.S. Cl.
CPC ......... *H04R 1/1016* (2013.01); *H04R 1/1041* (2013.01); *A61F 11/10* (2013.01); *H04R 25/45* (2013.01); *H04R 25/652* (2013.01); *H04R 25/656* (2013.01); *H04R 2225/61* (2013.01)

(58) Field of Classification Search
CPC ...... H04R 1/10; H04R 1/1008; H04R 1/1016; H04R 1/1041; H04R 25/656; H04R 25/652; H04R 25/45; H04R 2225/61; A61F 11/10; A61F 5/0096
See application file for complete search history.

(56) References Cited

U.S. PATENT DOCUMENTS

| 3,602,654 A | 8/1971 | Victoreen |
| 4,133,984 A * | 1/1979 | Akiyama ............. H04R 25/456 181/135 |
| 4,834,211 A * | 5/1989 | Bibby .................. H04R 25/652 181/130 |
| 5,682,020 A | 10/1997 | Oliveira |

(Continued)

FOREIGN PATENT DOCUMENTS

| KR | 101475265 | * 12/2014 | ............... H04R 1/10 |
| KR | 101475265 B1 | * 12/2014 | ............... H04R 1/10 |

(Continued)

OTHER PUBLICATIONS

Extended European Search Report Application No. 16178304.8, dated Dec. 19, 2016, 7 pages.

*Primary Examiner* — Oyesola C Ojo
(74) *Attorney, Agent, or Firm* — Artegis Law Group, LLP (57) ABSTRACT

One or more embodiments set forth include a personal aural device that includes an expandable eartip. The expandable eartip has a contracted state and an expanded state. The expandable eartip includes an insertion sensor configured to receive an indication that the eartip has been placed in an ear of a user. The expandable eartip further includes a controller configured to, in response, actuate a first device to inflate a first chamber to conform to a first portion of the ear. At least one advantage of the described techniques is that eartips in a set of earphones automatically inflate to provide an optimal fit for any listener's ears.

20 Claims, 7 Drawing Sheets

(56) References Cited

U.S. PATENT DOCUMENTS

| | | | |
|---|---|---|---|
| 5,953,435 A | 9/1999 | Mullin et al. | |
| 6,094,494 A | 7/2000 | Haroldson | |
| 6,393,130 B1* | 5/2002 | Stonikas | H04R 25/656 |
| | | | 181/135 |
| 6,704,428 B1* | 3/2004 | Wurtz | G10K 11/178 |
| | | | 381/370 |
| 6,810,987 B1 | 11/2004 | DeKalb | |
| 7,362,875 B2* | 4/2008 | Saxton | H04R 25/652 |
| | | | 381/322 |
| 8,270,649 B2* | 9/2012 | Semcken | H04R 25/656 |
| | | | 381/322 |
| 8,391,534 B2* | 3/2013 | Ambrose | H04R 1/1016 |
| | | | 128/864 |
| 8,526,651 B2* | 9/2013 | Lafort | H04R 25/60 |
| | | | 381/322 |
| 8,657,064 B2* | 2/2014 | Staab | H04R 25/656 |
| | | | 181/130 |
| 8,678,011 B2 | 3/2014 | Goldstein et al. | |
| 9,167,328 B2* | 10/2015 | Blendinger | H04R 25/656 |
| 9,338,568 B2* | 5/2016 | van Hal | H04R 25/652 |
| 2002/0196958 A1* | 12/2002 | Halteren | H04R 25/652 |
| | | | 381/328 |
| 2004/0215053 A1* | 10/2004 | Jorgensen | H04R 25/456 |
| | | | 600/25 |
| 2004/0258263 A1 | 12/2004 | Saxton et al. | |
| 2005/0094835 A1 | 5/2005 | Doty | |
| 2006/0098833 A1* | 5/2006 | Juneau | H04R 25/656 |
| | | | 381/328 |
| 2007/0116319 A1* | 5/2007 | Hagberg | H04R 1/1016 |
| | | | 381/380 |
| 2008/0099129 A1* | 5/2008 | Kuriyama | B32B 37/24 |
| | | | 156/155 |
| 2009/0022353 A1* | 1/2009 | Goldstein | A61F 11/10 |
| | | | 381/380 |
| 2009/0028356 A1* | 1/2009 | Ambrose | H04R 1/1016 |
| | | | 381/71.6 |
| 2009/0071486 A1* | 3/2009 | Perez | A61F 11/10 |
| | | | 128/858 |
| 2009/0101433 A1 | 4/2009 | Stiehl et al. | |
| 2009/0124286 A1* | 5/2009 | Hellfalk | H04M 1/6058 |
| | | | 455/556.1 |
| 2009/0285436 A1 | 11/2009 | Lowry | |
| 2010/0002897 A1* | 1/2010 | Keady | A61F 11/10 |
| | | | 381/328 |
| 2010/0322454 A1* | 12/2010 | Ambrose | H04R 1/1016 |
| | | | 381/380 |
| 2011/0066176 A1* | 3/2011 | Coole | A61B 17/56 |
| | | | 606/198 |
| 2012/0155689 A1* | 6/2012 | Milodzikowski | H04R 1/1016 |
| | | | 381/379 |
| 2013/0092470 A1* | 4/2013 | Johnston | H04R 1/1016 |
| | | | 181/129 |
| 2013/0101147 A1* | 4/2013 | Kraemer | H04R 1/1016 |
| | | | 381/322 |
| 2013/0121494 A1* | 5/2013 | Johnston | H04R 1/1041 |
| | | | 381/56 |
| 2013/0136285 A1* | 5/2013 | Naumann | H04R 1/1016 |
| | | | 381/329 |
| 2013/0251172 A1* | 9/2013 | Mosseri | H04R 1/1083 |
| | | | 381/74 |
| 2013/0272530 A1 | 10/2013 | Gauger, Jr. | |
| 2013/0317576 A1* | 11/2013 | Rogers | A61F 7/007 |
| | | | 607/99 |
| 2014/0037123 A1 | 2/2014 | Tan et al. | |
| 2014/0119585 A1* | 5/2014 | van Hal | H04R 25/652 |
| | | | 381/330 |
| 2014/0146976 A1* | 5/2014 | Rundle | H04R 1/1083 |
| | | | 381/71.6 |
| 2015/0282990 A1* | 10/2015 | Krause | A61F 11/10 |
| | | | 128/865 |
| 2016/0050483 A1* | 2/2016 | Kulavik | H04R 1/1041 |
| | | | 381/380 |
| 2016/0166203 A1* | 6/2016 | Goldstein | A61B 5/6817 |
| | | | 600/301 |

FOREIGN PATENT DOCUMENTS

| | | |
|---|---|---|
| WO | 2009015210 A2 | 1/2009 |
| WO | 2009055347 A2 | 4/2009 |

* cited by examiner

EARTIP THAT CONFORMS TO A USER'S EAR CANAL

BACKGROUND

Field of the Embodiments of the Present Disclosure

Embodiments of the present disclosure relate generally to personal aural devices and, more specifically, to an eartip that conforms to a user's ear canal.

Description of the Related Art

Various ear-mounted devices are in popular use for various applications. Passive earplug devices are used to block out noise and other distracting sounds from reaching the ear. In addition, earphones are an increasingly popular accessory for personal audio listening. Typically, earphones include an audio plug for insertion into an audio output of an audio playback device, also referred to herein as a personal audio device. The audio plug connects to a cable that carries the audio signal from the audio playback device to a pair of eartips, also referred to herein as earbuds, that are inserted into the listener's, or user's, ears. Alternatively, the earphones and personal audio device form a wireless connection, such as a Bluetooth connection, whereby the audio signal is transmitted from the personal audio device to a receiver associated with the earphones. With some earphones, the eartips are supplied having a single size and shape that is designed to fit into the average listener's ears. With other earphones, the eartips are supplied in multiple sizes and shapes, where a listener selects the eartips that best fit the listener's ears.

One potential problem with these approaches is that even when multiple eartips are supplied, the supplied eartips often do not provide an optimal fit for a given listener. As a result, the eartips do not provide a good acoustic seal, causing audio signal leakage and a reduction in the quality of the listener's experience, particularly with respect to bass response. Another potential problem with these approaches is that ill-fitting eartips are often uncomfortable and can easily fall out of the listener's ears as the listener performs various activities.

One possible solution to these potential problems is to provide custom eartips designed for a specific listener. For example, eartips could be made of a material that becomes pliable when placed in warm water. The listener would place the eartips in warm water for a few minutes, and then would place the eartips snugly into his or her ears. As the eartips cool, the eartips would conform to the outer portion of the listener's ear canals. Alternatively, the listener could visit an audiologist who could create an impression, or mold, of the listener's ear canals. The audiologist, or an associated laboratory, would fabricate a custom set of eartips for the listener based on the impression. One drawback with these possible solutions is that such eartips are only usable by a single listener and are effectively unusable by anyone else. Another drawback with these solutions is that the shape of the listener's ear canals is subject to change as the listener ages. As a result, eartips that originally provided an optimal fit for a given listener eventually provide a suboptimal fit with the passage of time.

Another possible solution to the above problems is to provide eartips that have a multiple flanged system, where there listener inserts the eartip until one of the flanges fits snugly against the entrance of the ear canal. But an eartip with such a multiple flanged system typically extends deeply into the ear canal, causing increased discomfort to the listener when wearing the eartip.

As the foregoing illustrates, a new technique for fitting eartips to a listener's ears would be useful.

SUMMARY

One or more embodiments set forth include a personal aural device that includes an expandable eartip. The expandable eartip has a contracted state and an expanded state. The expandable eartip includes an insertion sensor configured to receive an indication that the eartip has been placed in an ear of a user. The expandable eartip further includes a controller configured to, in response, actuate a first device to inflate a first chamber to conform to a first portion of the ear.

Other embodiments include, without limitation, an eartip device that implements one or more aspects of the disclosed techniques, and a computer readable medium including instructions for performing one or more aspects of the disclosed techniques, as well as a method for performing one or more aspects of the disclosed techniques.

At least one advantage of the approach described herein is that eartips in a set of earphones automatically inflate to provide an optimal fit for any listener's ears. As a result, the quality of the listener's audio experience is improved, and the potential for the eartips to cause discomfort or to fall out of the listener's ears is reduced.

BRIEF DESCRIPTION OF THE SEVERAL VIEWS OF THE DRAWINGS

So that the manner in which the recited features of the one more embodiments set forth above can be understood in detail, a more particular description of the one or more embodiments, briefly summarized above, may be had by reference to certain specific embodiments, some of which are illustrated in the appended drawings. It is to be noted, however, that the appended drawings illustrate only typical embodiments and are therefore not to be considered limiting of its scope in any manner, for the scope of the invention subsumes other embodiments as well.

DETAILED DESCRIPTION

In the following description, numerous specific details are set forth to provide a more thorough understanding of certain specific embodiments. However, it will be apparent to one of skill in the art that other embodiments may be practiced without one or more of these specific details or with additional specific details.

System Overview

Figure 1A:
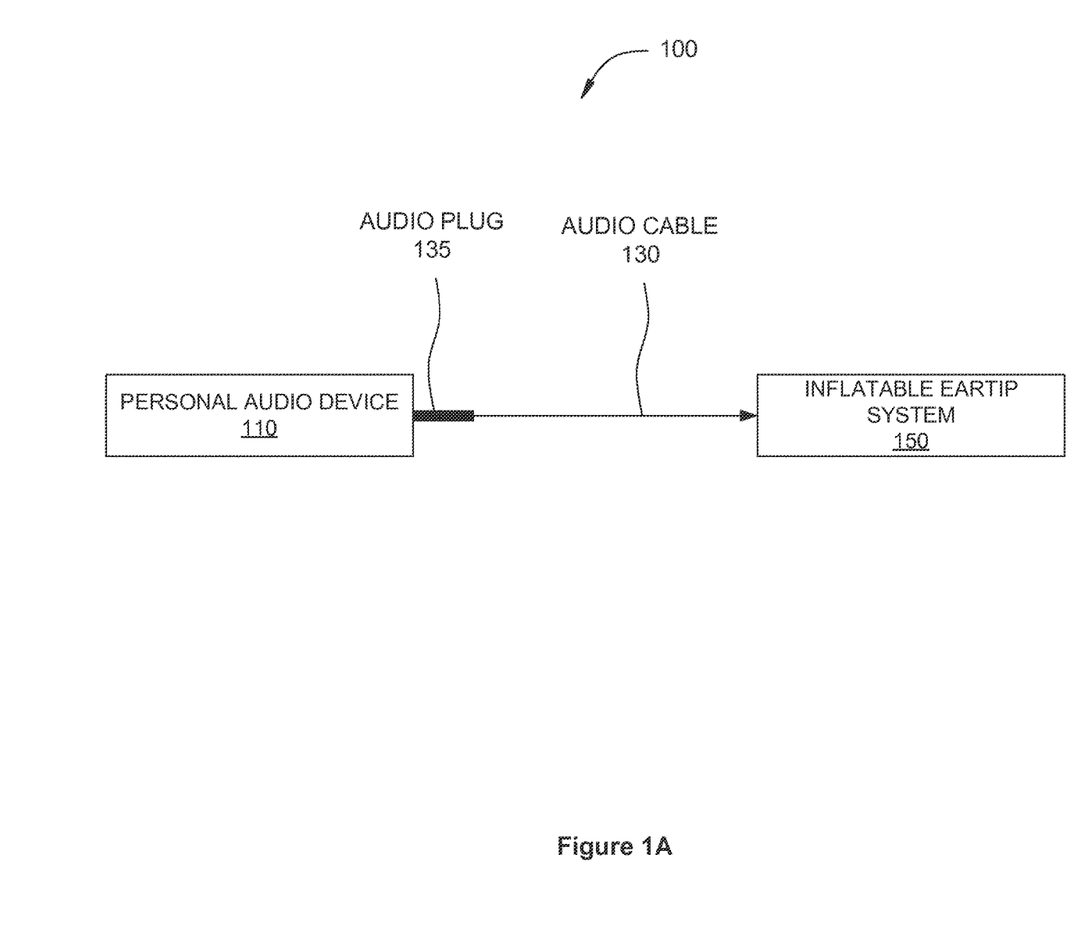
FIG. 1A illustrates a personal audio device associated with an inflatable eartip system, according to various embodiments.

FIG. 1A illustrates a personal audio listening system 100, according to various embodiments. As shown, the personal audio listening system 100 includes a personal audio device 110 and an inflatable eartip system 150 connected via an audio cable 130. The personal audio listening system 100 is also referred to herein as a personal headphone system.

Personal audio device 110 is any device configured to deliver audio to headphones or earphones via an audio jack (not explicitly shown). Personal audio device 110 may also have internal speakers (not explicitly shown) for audio playback. Typically, such internal speakers are disabled when audio is being delivered to headphones or earphones. Personal audio device 110 may be any technically feasible device, including, without limitation, a mobile audio player, a smartphone, a tablet computer, and a gaming console.

Audio cable 130 receives audio from personal audio device 110 and delivers the received audio to inflatable eartip system 150. Typically, audio cable 130 includes an audio plug 135 at one end. Audio plug 135 is configured to be inserted into a corresponding audio jack on personal audio device 110. In some embodiments, insertion of audio plug 135 into an audio jack on personal audio device 110 disables internal speakers included within personal audio device 110, if any. In some embodiments, personal audio device 110 may connect wirelessly with inflatable eartip system 150, such as via a Bluetooth connection or other wireless connection. In some embodiments, personal audio device 110 may connect with inflatable eartip system 150 as a digital data transfer, such as via a micro USB or other data connection Inflatable eartip system 150 receives audio from personal audio device 110 via audio cable 130. As further described herein, inflatable eartip system 150 is configured to detect when an eartip is inserted into a listener's ear, and automatically expand the eartip to conform to an ear of the listener. Inflatable eartip system 150 includes one or more inflatable chambers that expand in order to form an acoustic seal, to retain the eartip in the ear of the listener, or to both form an acoustic seal and retain the eartip. Examples described herein include an inflatable eartip system with one inflatable chamber, as well as an inflatable eartip system with two inflatable chambers. However, inflatable eartip system 150 can include three or more inflatable chambers, within the scope of the present disclosure. In embodiments with three or more inflatable chambers, the series of chambers may resemble a multiple flanged eartip, which may provide a higher quality seal for blocking ambient noise relative to eartips with fewer chambers. Although illustrated as a single system, inflatable eartip system 150, in some embodiments, may include two independent eartip systems, corresponding to the left ear and the right ear of the listener. Inflatable eartip system 150 is now described in further detail.

Figure 1B:
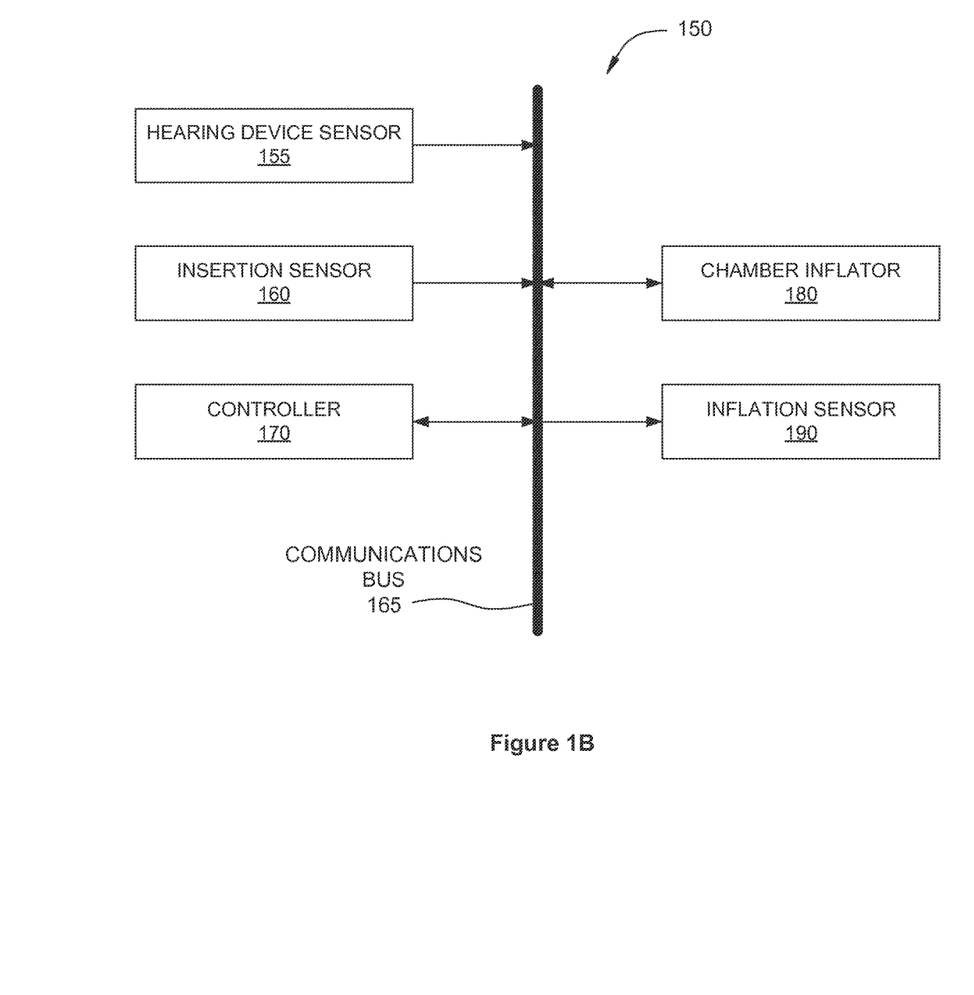
FIG. 1B illustrates the inflatable eartip system of FIG. 1A, according to various embodiments.

FIG. 1B illustrates the inflatable eartip system 150 of FIG. 1A, according to various embodiments. As shown, the inflatable eartip system includes, without limitation, a hearing device 155, an insertion sensor 160, a controller 170, a chamber inflator 180, and an inflation sensor 190, coupled together via a communications bus 165.

Hearing device 155 may be any technically feasible device, such as a speaker, for transforming an electrical signal received via an electrical wire (not explicitly shown) into an acoustic signal that is detectable by the listener.

Insertion sensor 160 may be any technically feasible device configured to determine that one or both eartips are properly inserted in the listener's ears. In one example, and without limitation, insertion sensor 160 could detect skin contact at or near the inflatable membrane of the eartip. Insertion sensor 160 could detect skin contact via any technically feasible approach, including, without limitation, one or more capacitive touch sensors. In another example, and without limitation, insertion sensor 160 could detect a change in lighting conditions, such as a reduction in light on an inner portion of the eartip when the eartip is inserted in the listener's ear. Insertion sensor 160 could detect when both earbuds are powered on or otherwise receiving audio, no or low degree of light is detected on the inside edge of the eartip, and a relatively higher degree of light is detected on the outside edge of the eartip. In another example, and without limitation, insertion sensor 160 could include a pressure sensor that detects when pressure is applied to the inflatable eartip system 150 by the ear canal of the listener. In yet another example, and without limitation, insertion sensor 160 could detect when one or both eartips are in a specific orientation. Insertion sensor 160 could detect that one or both eartips are positioned in a particular orientation, such as a horizontal orientation. Insertion sensor 160 could detect the particular orientation via any technically feasible approach, including, without limitation, a tilt sensor, a position sensor, or an accelerometer. If insertion sensor 160 includes a position sensor, then such a position sensor could include an ultrasonic sensor or other sensor that could determine when the eartip is resting on another surface. Such sensors could be arranged axially within the ear canal to determine when the eartip is placed into the ear canal.

In another example, and without limitation, insertion sensor 160 could detect when the eartips are facing each other, such as by passing a signal between the eartips or by detecting presence of the other eartip through the skull of the listener. In yet another example, and without limitation, insertion sensor 160 could detect when music or another audio signal is passing through the hearing device associated with the eartip. In yet another example, and without limitation, insertion sensor 160 could detect closure of switch contacts when the eartip is fully inserted in the listener's ear. Insertion sensor 160 could detect switch closure via any technically feasible approach, including, without limitation, a sliding contact that engages when the eartip is fully inserted.

In yet another example, and without limitation, insertion sensor 160 could employ any technically feasible combination of the approaches described herein. For example, and without limitation, insertion sensor 160 could detect when an audio signal is passing through the hearing device of the eartip, the eartip is horizontally oriented, and detected light on the inner portion of the eartip is low relative to the outer portion of the eartip. In yet another example, and without limitation, the eartip may be fitted with a manual pump (not explicitly shown) rather than insertion sensor 160. The manual pump could include a manual button to pump air into a chamber of the eartip after the eartip is inserted into the listener's ear. The manual button could also include a mechanism to release air from the chamber to effectuate removal of the eartip from the listener's ear. In yet another example, and without limitation, the eartip may be fitted with a pump (not explicitly shown) that is controllable via a remote control, such as a wireless electronic button that, when pressed, transmits a signal that causes the manual pump to pump air into a chamber of the eartip after the eartip is inserted into the listener's ear.

Controller 170 may be any technically feasible device configured to receive signals from insertion sensor 160 and inflation sensor 190 and to transmit signals to chamber inflator 180. For example, controller 170 could receive a signal from insertion sensor 160 indicating that the eartip is inserted in the listener's ear. In response, controller 170 could transmit a signal to chamber inflator 180 to begin to inflate one or more chambers within the eartip. Subsequently, controller 170 could receive a signal from inflation sensor 190 indicating that the chamber(s) of the eartip are sufficiently inflated. In response, controller 170 could transmit a signal to chamber inflator 180 to stop inflating one or more chambers within the eartip. In some embodiments, controller 170 may further process signals received from insertion sensor 160 and inflation sensor 190 to ensure proper operation of the eartip.

By way of example, and without limitation, controller 170 could receive a signal from inflation sensor 160 indicating that music or other audio is passing through the hearing device. In response, controller 170 could transmit a signal to chamber inflator 180 to inflate the eartip chambers. Alternatively, controller 170 could combine the condition of audio passing through the hearing device with one or more additional signals received from inflation sensor 160 indicating skin contact, a change in lighting condition, closure of switch contacts, etc., as further described herein. Such an approach would reduce the likelihood of prematurely inflating the eartip chambers when a listener starts to play audio through the hearing device prior to inserting the eartip into the listener's ear. Subsequently, controller 170 could receive a signal from inflation sensor indicating that audio is no longer passing through the hearing device. In response, controller 170 could wait for a specific period of time before transmitting a signal to chamber inflator 180 to deflate the eartip chambers. By waiting for a period of time, controller 170 does not deflate the eartip chambers for typical length gaps between consecutive songs.

In various embodiments, controller 170 may be a state machine, a central processing unit (CPU), digital signal processor (DSP), an application-specific integrated circuit (ASIC), or any device or structure configured to process data and execute software applications.

Chamber inflator 180 may be any technically feasible device configured to inflate and deflated one or more chambers within the eartip in response to receiving a signal from controller 170. Chamber inflator 180 may inflate and deflated the chambers by respectively pressurizing and depressurizing the chambers. In one example, and without limitation, chamber inflator 180 could be a pneumatic or hydraulic pump that would compress a fluid, such as atmospheric air, and inject the compressed fluid into the chambers. In particular, atmospheric air has certain advantageous characteristics in that air is lightweight, is easily exchangeable with the environment, and is relatively easy to compress and move via the mechanical movement of a pump. Alternatively, chamber inflator could compress and inject an alternative fluid, whether the fluid is a gas or a liquid. Such a pump could be mechanical or electrical, such as a microblower that generates ultrasonic vibrations via piezoelectric ceramics.

In another example, and without limitation, chamber inflator 180 could transmit an electric signal that would align fibers embedded in or otherwise in contact with the chambers, where the aligning of the fibers causes the chamber to expand, a process referred to herein as electrostatic flocking.

In yet another example, and without limitation, chamber inflator 180 could employ one or more other techniques to cause the eartip chambers to inflate or expand, such as magnetostriction, electrostriction of dielectrics, or a reversible chemical reaction. In yet another example, and without limitation, chamber inflator 180 could include a manual pump with a button for inflating and deflating the eartip chambers, as further described herein.

In some embodiments, chamber inflator 180 may include a limiter or governor that prevents chamber inflator 180 from developing a pressure greater than a specified threshold level. In other embodiments, chamber inflator 180 may operate for a set amount of time. In addition, the eartip chambers could include a valve or leakage baffle that release pressure when the pressure within the eartip chambers exceeds a specified threshold level.

Inflation sensor 190 may be any technically feasible device configured to determine that one or more chambers in the eartip are sufficiently inflated. In one example, and without limitation, inflation sensor 190 could detect that the pressure within the eartip chambers has reached a threshold level. In another example, and without limitation, inflation sensor 190 could detect a change in an operating condition of chamber inflator 180 indicating that that the eartip chamber is sufficiently inflated. After chamber inflator 180 sufficiently inflates the eartip chambers, back pressure or the operating limits of chamber inflator 180 could cause chamber inflator 180 to draw an increased amount of electric current. Alternatively, chamber inflator 180 could emit an acoustic sound during operation, where the frequency of the acoustic sound increases or decreases when chamber inflator 180 nears an operating limit. A microphone or similar device could detect such a change in acoustic frequency, thereby detecting that the eartip chamber is sufficiently inflated.

In yet another example, and without limitation, inflation sensor 190 could employ any technically feasible combination of the approaches described herein. For example, and without limitation, inflation sensor 190 could detect when the pressure in the eartip chambers has reached a specified threshold and when a change in an operating characteristic of chamber inflator 180 has occurred. Either one or both of these conditions could indicate that the eartip chamber is sufficiently inflated.

Persons skilled in the art will understand that the specific implementation of the eartip system 150 shown in FIG. 1B are provided for exemplary purposes only, and not meant to limit the scope of the present invention. In practice, eartip system 150 may be implemented by a wide variety of different combinations of hardware and software. For example, and without limitation, eartip system 150 could be implemented by an integrated circuit configured to perform the functionality described above, without limitation. In another example, and without limitation, eartip system 150 could be implemented by a state machine, microcontroller, or system-on-chip configured to perform that functionality, without limitation. As a general matter, any device configured to perform the functionality of eartip system 150 described herein falls within the scope of the present invention. Similarly, eartip system 150 may be configured to perform any technically feasible approach for adjusting an eartip associated with a personal audio device to conform the eartip to a listener's ear.

Operations of the Eartip with Inflatable Chambers

Figure 2:
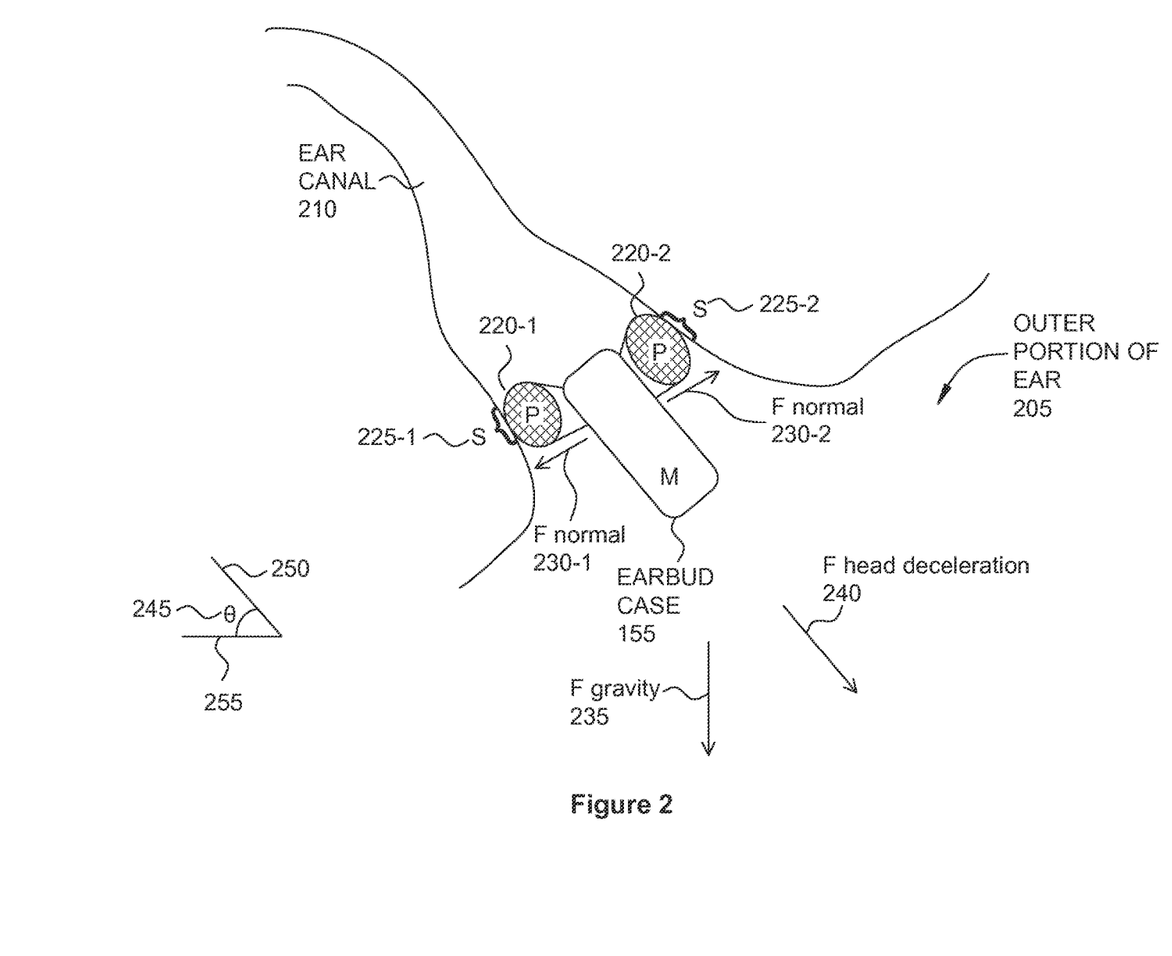
FIG. 2 is an embodiment of the eartip system of FIG. 1B with one inflatable chamber.

FIG. 2 is an embodiment of the eartip system of FIG. 1B with one inflatable chamber. As shown, an outer portion of an ear 205 and ear canal 210 are illustrated in cutaway view. As also shown, the hearing device 155 of FIG. 1B is surrounded by an inflatable chamber 220-1, 220-2, and inserted into the ear canal 210.

Inflatable chamber 220-1, 220-2 when deflated, allows hearing device 155 to be inserted into the ear canal 210. When inflated, inflatable chamber 220-1, 220-2 forms an acoustic seal between hearing device 155 and the ear canal 210. In the inflated state, inflatable chamber 220-1, 220-2 allows acoustic signals to pass from hearing device 155 to the ear canal 210, while substantially preventing acoustic signals present in and around the outer portion of the ear 205 from entering the ear canal 210.

When inflated, inflatable chamber 220-1, 220-2 forms a contact surface 225-1, 225-2 with the ear canal 210. In one example, and without limitation inflatable chamber 220-1, 220-2 could be portions of a single continuous chamber. In another example, and without limitation, inflatable chamber 220-1 and inflatable chamber 220-2 could be exemplary sub-chambers in a set of two or more separately inflatable sub-chambers that are coupled together. As shown, inflatable chamber 220-1 contacts surface 225-1 of the ear canal 210, causing a normal force $F_{normal}$ 230-1 to be exerted on surface 225-1. Likewise, inflatable chamber 220-2 contacts surface 225-2 of the ear canal 210, causing a normal force $F_{normal}$ 230-2 to be exerted on surface 225-2. In some embodiments, inflatable chamber 220-1, 220-2 may contact the ear at specific contact points, such as the tragus and antitragus (not explicitly shown), and not form a seal around the entire ear canal. Such an open design allows environmental sounds to enter the ear canal while still providing retention capability. In other embodiments, inflatable chamber 220-1, 220-2 may be in a substantially toroidal shape, or some other appropriate shape, forming a continuous contact surface 225-1, 225-2 with the ear canal 210. In yet other embodiments, inflatable chamber 220-1, 220-2 may be in a substantially toroidal shape to form a continuous contact surface with the ear canal and, in addition, have increased contact with the tragus and the antitragus. In these embodiments, the total contact surface area is increased, relative to the other described embodiments, allowing for lower inflation pressure for the same retention capability. As a result, retention capability may be improved with little or no increase in listener discomfort. In one example, and without limitation inflatable chamber 220-1, 220-2 could be a single continuous chamber.

As shown, the outer portion of the ear 205 and ear canal 210 are angled downward, forming an angle θ 245, where angle θ 245 is measured between a first line 250 that is substantially parallel to the ear canal 210 and a second line 255 that is horizontal to the ground. When the outer portion of the ear 205 and ear canal 210 are placed at such an angle, two forces operate together that tend to cause hearing device 155 to become dislodged from the ear canal 210. The first force is a gravitational force $F_{gravity}$ 235 associated with the earth's gravitational force. Gravitational force varies with the angle θ 245 of the ear canal 210 with respect to the ground, increasing for the downward positioned ear as the head is tilted from vertical to horizontal. The second force is a head motion force $F_{motion}$ 240 in the direction of the ear canal resulting from movement of the listener's head. For example, and without limitation $F_{motion}$ and caused when the listener tilts and moves his or her head. Head motion force $F_{motion}$ 240 is relatively small during light activities, such as when a listener slowly bends over, and relatively large during more vigorous activities, such as when an athlete quickly changes lateral direction. The gravitational force $F_{gravity}$ 235 and the head motion force $F_{motion}$ 240 are combined to form a total outward force $F_{outward}$ on hearing device 155 and inflatable chamber 220-1, 220-2, as given by Equations 1-2 below:

$$F_{outward} = F_{gravity} - F_{motion} \quad (1)$$

$$F_{outward} = M_{eartip} * A_{gravity} \sin(\theta) - M_{eartip} * A_{motion} \quad (2)$$

where $M_{eartip}$ is the mass of the entire eartip (including hearing device 155 and inflatable chamber 220-1, 220-2), $A_{gravity}$ is the acceleration due to gravity, sin(θ) is the sine of angle θ 245, and $A_{motion}$ is the acceleration due to head motion.

In order to counter this outward force $F_{outward}$, and thus prevent the eartip from dislodging from the ear canal 210, the friction force $F_{friction}$ exerted onto the ear canal 210 by inflatable chamber 220-1, 220-2 should be greater than or equal to or greater than the outward force $F_{outward}$, per Equation (3) below:

$$F_{friction} \geq F_{outward} \quad (3)$$

where the friction force $F_{friction}$ is given by Equation (4) below:

$$F_{friction} \leq \mu_{static\_friction} * F_{normal} \quad (4)$$

where $\mu_{static\_friction}$ is the coefficient of static friction between inflatable chamber 220-1, 220-2 and the ear canal 210, and $F_{normal}$ is the normal force, described above.

The coefficient of static friction $\mu_{static\_friction}$ depends on the material of inflatable chamber 220-1, 220-2 and on the skin on the human ear. In some embodiments, the coefficient of static friction $\mu_{static\_friction}$ may further depend on various environmental conditions, including, without limitation, humidity, temperature, and perspiration present on the skin of the listener's ear. As seen in Equation (4), for a given $F_{friction}$, increasing the coefficient of static friction $\mu_{static\_friction}$ allows for a lower normal force $F_{normal}$. In other words, if inflatable chamber 220-1, 220-2 is fabricated from a tacky or sticky material with a relatively high coefficient of static friction $\mu_{static\_friction}$, such as a thin silicone rubber membrane, a lower normal force $F_{normal}$ could be applied to the ear canal 210 to achieve the desired $F_{friction}$. Typically, a lower normal force $F_{normal}$ applied to the ear canal 210 results in less discomfort for the user. Such a silicone rubber membrane would stretch easily and is tacky when placed against the skin, resulting in a relatively a high coefficient of static friction. When inflated, the silicone rubber membrane would be sealed against the ear canal.

The normal force $F_{normal}$ is calculated as the normal inflation pressure of inflatable chamber 220-1, 220-2 $P_{normal}$ multiplied by the contact surface area between S inflatable chamber 220-1, 220-2 and the ear canal 210. Generally, the contact surface area is small at lower pressures, and increases as the pressure increases until the contact surface area increases to a maximum level at full inflation. The normal force $F_{normal}$ is calculated according to Equation (5) below:

$$F_{normal} = P_{normal} * S \quad (5)$$

The minimum normal inflation pressure needed to prevent the eartip from dislodging is calculated by combining Equations (2), (3), (4), and (5), as shown by Equation (6) below:

$$P_{normal} = M_{eartip} * (A_{gravity} \sin(\theta) - A_{motion}) / (S * \mu_{static\_friction}) \quad (6)$$

Figure 3A:
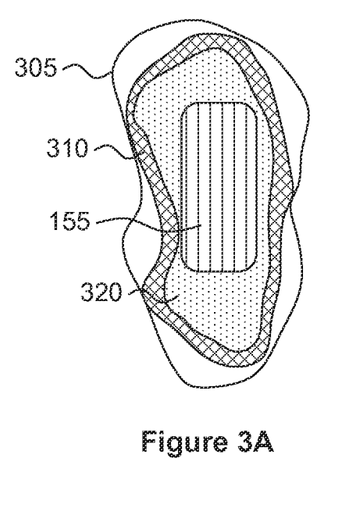
FIGS. 3A-3B illustrate the eartip system of FIG. 2 in different operating states, according to various embodiments.
Figure 3B:
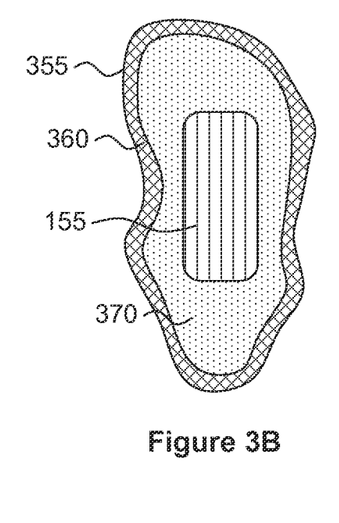

FIGS. 3A-3B illustrate the eartip system of FIG. 2 in different operating states, according to various embodiments. In particular, FIG. 3A illustrates the eartip system in a deflated, contracted, or unpressurized state, and FIG. 3B illustrates the eartip system in an inflated, expanded, or pressurized state.

As shown in FIG. 3A, an inflatable chamber 310 surrounds eartip material 320 and a hearing device 155. Because inflatable chamber 310 is in a deflated state, hearing device 155 is easily inserted into the ear canal 305. In the deflated state, gaps exist between the ear canal 305 and inflatable chamber 310 to accommodate insertion. In this deflated state, inflatable chamber 310 does not form an acoustic seal between hearing device 155 and the ear canal 305. Further, in the deflated state, inflatable chamber 310 does not retain hearing device 155 from dislodging.

As shown in FIG. 3B, an inflatable chamber 360 surrounds eartip material 370 and a hearing device 155. Because inflatable chamber 360 is in an inflated state, hearing device 155 is easily retained in the ear canal 355, so that hearing device 155 does not become dislodged during normal activities. In the inflated state, substantially no gaps exist between the ear canal 355 and inflatable chamber 360. In this inflated state, inflatable chamber 310 forms a strong acoustic seal between hearing device 155 and the ear canal 355.

The eartip illustrated in FIGS. 2-3 provides a good acoustic seal as well as moderate retention capabilities. However, the eartip of FIGS. 2-3 is subject to becoming dislodged if the listener engages in more vigorous activities. Although $P_{normal}$ could be increased to improve retention capability, applying too much pressure to the ear canal is likely to cause great discomfort to the listener. The concha of the outer portion of the ear is generally more tolerant of pressure than the ear canal. Further, the concha has significantly more surface area, and, as a result, provides greater retention capability at the same or lower pressure, relative to the ear canal. Therefore, in an embodiment, an eartip may include a first inflatable chamber to form a strong acoustic seal with the ear canal and a second inflatable chamber to form a strong retention capability with the outer portion of the ear. This embodiment is now described.

Figure 4:
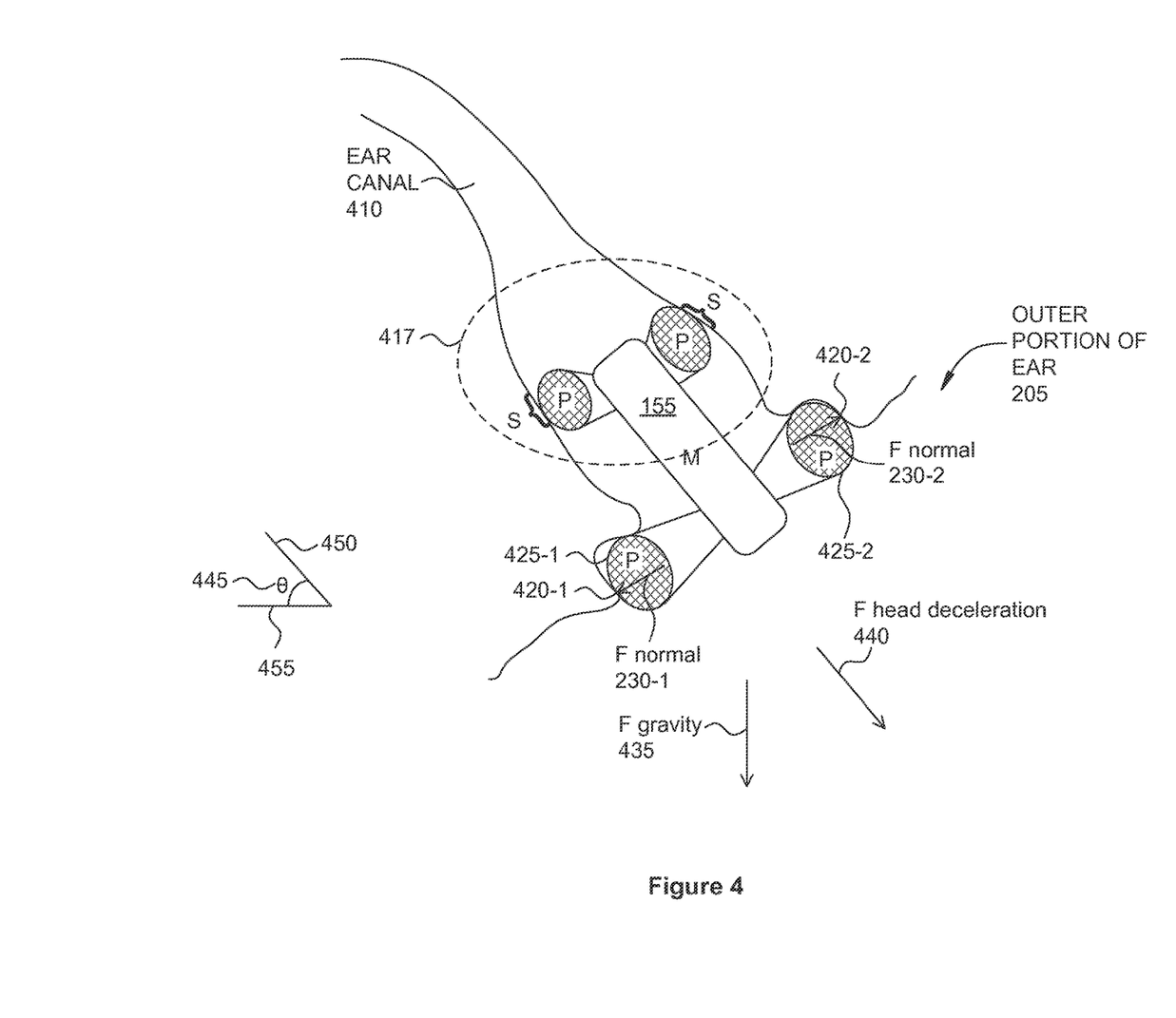
FIG. 4 is an embodiment of the eartip system of FIG. 1B with two inflatable chambers.

FIG. 4 is an embodiment of the eartip system of FIG. 1B with two inflatable chambers. As shown, an outer portion of an ear 405 and ear canal 410 are illustrated in cutaway view. As also shown, the hearing device 155 of FIG. 1B is surrounded by a first inflatable chamber 417 inserted into the ear canal 410, and a second inflatable chamber 420-1, 420-2 inserted into the concha (not explicitly shown) of the outer portion of the ear 405.

First inflatable chamber 417 functions substantially as described in conjunction with FIGS. 2-3 above. When both first inflatable chamber 417 and second inflatable chamber 420-1, 420-2 are deflated, hearing device 155 is easily inserted into the ear canal 410 and outer portion of the ear 405, respectively. When inflated, first inflatable chamber 417 forms a strong acoustic seal with the ear canal 410. First inflatable chamber 417 also provides some retention capability to prevent hearing device 155 from dislodging. When inflated, second inflatable chamber 420-1, 420-2 forms a strong retention bond with the concha of the outer portion of the ear 405. Second inflatable chamber 420-1, 420-2 also provides some additional acoustic seal for hearing device 155.

When inflated, inflatable chamber 420-1, 420-2 forms a contact surface 425-1, 425-2 with the ear canal 410. In one example, and without limitation inflatable chamber 420-1, 420-2 could be portions of a single continuous chamber. In another example, and without limitation, inflatable chamber 420-1 and inflatable chamber 420-2 could be exemplary sub-chambers in a set of two or more separately inflatable sub-chambers that are coupled together. As shown, inflatable chamber 420-1 contacts surface 425-1 of the concha of the outer portion of the ear 405, causing a normal force $F_{normal}$ 430-1 to be exerted on surface 425-1. Likewise, inflatable chamber 420-2 contacts surface 425-2 of the concha of the outer portion of the ear 405, causing a normal force $F_{normal}$ 430-2 to be exerted on surface 425-2. In some embodiments, inflatable chamber 420-1, 420-2 may contact the concha of the outer portion of the ear 405 at specific contact points. In other embodiments, inflatable chamber 420-1, 420-2 may be in a substantially toroidal shape, or some other appropriate shape, forming a continuous contact surface 425-1, 425-2 with the concha of the outer portion of the ear 405.

As shown, the outer portion of the ear 405 and ear canal 410 are angled downward, forming an angle θ 445, where angle θ 445 is measured between a first line 450 that is substantially parallel to the ear canal 410 and a second line 455 that is horizontal to the ground. When the outer portion of the ear 405 and ear canal 410 are placed at such an angle, two forces operate together that tend to cause hearing device 155 to become dislodged from the ear canal 410, namely a gravitational force $F_{gravity}$ 435 associated with the earth's gravitational force and a head motion force $F_{motion}$ 440 in the direction of the ear canal and caused when the listener tilts and moves his or her head. The force equations for inflatable chamber 420-1, 420-2 are given by Equations (1)-(6), as further discussed herein in conjunction with FIG. 2.

Figure 5A:
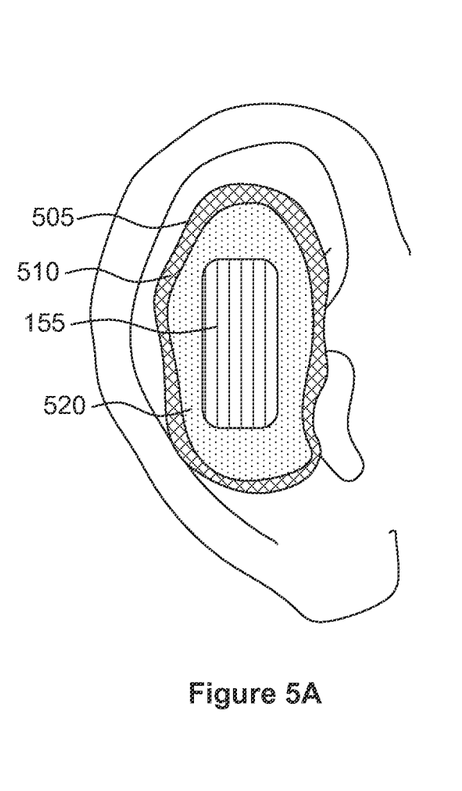
FIGS. 5A-5B illustrate the eartip system of FIG. 4 in different operating states, according to various embodiments.
Figure 5B:
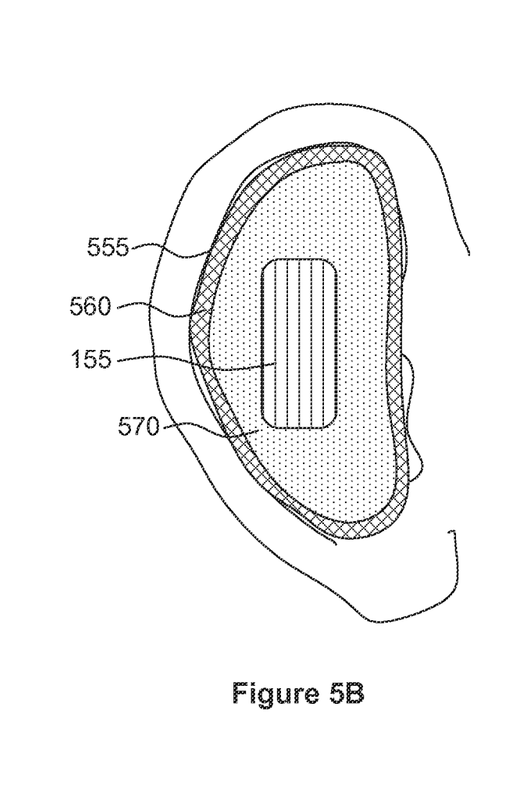

FIGS. 5A-5B illustrate the eartip system of FIG. 4 in different operating states, according to various embodiments. In particular, FIG. 5A illustrates the eartip system in a deflated, contracted, or unpressurized state, and FIG. 5B illustrates the eartip system in an inflated, expanded, or pressurized state.

As shown in FIG. 5A, an inflatable chamber 510 surrounds eartip material 520 and a hearing device 155. Because inflatable chamber 510 is in a deflated state, hearing device 155 is easily inserted into the concha of the outer portion of the ear 505. In the deflated state, gaps exist between the outer portion of the ear 505 and inflatable chamber 510 to accommodate insertion. In this deflated state, inflatable chamber 510 does not form a retention capability between hearing device 155 and the outer portion of the ear 505. The inner inflatable chamber that creates an acoustic seal with the ear canal is not visible in the view illustrated by FIG. 5A.

As shown in FIG. 5B, an inflatable chamber 560 surrounds eartip material 570 and a hearing device 155. Because inflatable chamber 560 is in an inflated state, hearing device 155 is easily retained in the outer portion of the ear 555, so that hearing device 155 does not become dislodged during normal activities. In the inflated state, substantially no gaps exist between the outer portion of the ear 555 and inflatable chamber 560. In this inflated state, inflatable chamber 310 forms a strong retention capability between hearing device 155 and the outer portion of the ear 555. The inner inflatable chamber that creates an acoustic seal with the ear canal is not visible in the view illustrated by FIG. 5B.

As illustrated in FIGS. 4-5, a two-chamber eartip provides a first inflatable chamber for a strong acoustic seal with the ear canal of the listener and a second inflatable chamber for a strong retention capability with the concha of the outer portion of the ear. In some embodiments, a listener may desire strong retention capability along with a need or desire to hear sounds from the environment. The listener may want to hear environmental sounds, including, without limitation, sounds from machinery operating nearby, traffic sounds, other pedestrians, runners and cyclists, and voices of co-workers. In such embodiments, an eartip may employ a single inflatable chamber to engage with the concha of the outer portion of the ear for strong retention capability and no inflatable chamber to engage with the ear canal. Such an eartip may allow at least some environmental sounds to pass from the outer portion of the ear into the ear canal.

Persons skilled in the art will understand that the exemplary use-case scenarios described above in conjunction with FIGS. 2-5 are provided for exemplary purposes only to illustrate different techniques personal audio device 110 may implement to conform an eartip to a listener's ear. Many other configurations of a personal audio device, each with one or more inflatable chambers, may be implemented using the described techniques, within the scope of this disclosure. Further, the examples discussed above, although presented with reference to specific commands, devices, and operations, are not meant to limit the scope of the invention to those specificities.

In one example, and without limitation, the techniques described herein could be deployed in association with any personal aural devices, including, without limitation, passive ear-protection earplugs, active earplugs, wired earphones, wireless earphones, in-ear monitors, interruptible foldback (IFB) devices, hearing aids, health monitoring devices, and any ear-mounted receiver or transmitter. In another example, and without limitation, the techniques described herein could be deployed with a personal aural device that includes any technically feasible quantity of inflatable chambers, including, without limitation, a single inflatable chamber, two inflatable chambers, and three or more inflatable chambers. In yet another example, and without limitation, one or more inflatable chambers could form a more or less continuous contact surface with the ear when inflated. Alternatively, one or more inflatable chambers could expand at particular positions relative to the ear so as to avoid nerve rich areas of the ear. In this manner, a higher normal force could be applied at ear positions with relatively fewer nerve endings, resulting in relatively higher retention capability while not causing the listener to experience discomfort.

In yet another example, and without limitation, different personal aural devices could be fitted with bladders of different sizes of inflatable chambers. Such personal aural devices could accommodate vastly different ear sizes, where a smaller chamber could accommodate a range of relatively smaller ear sizes and a larger chamber could accommodate a range of relatively larger ear sizes. This approach reduces the likelihood that a smaller chamber cannot sufficiently inflate to seal against a larger ear without tearing or a larger chamber wrinkles and, thereby, makes a relatively poor acoustic seal within a smaller ear. The inflatable chambers could be replaced by the listener, either to better fit the personal aural device to the listener or to replace a damaged chamber. In yet another example, and without limitation, the amount of inflation pressure of one or more inflatable chambers could be adjustable by the listener. Such an approach could accommodate different listeners who could have different preferences and tolerances for the amount of pressure applied to the ears. In this manner, a listener could control the inflation pressure to a customizable balance between comfort, fit, and acoustic seal. In yet another example, and without limitation, a personal aural device could be fitted with multiple separately controlled inflatable chambers, whereby some chambers could be inflated while other chambers could remain non-inflated. Similarly, an inflatable chamber could be fitted with multiple separately controlled inflatable sub-chambers, whereby some sub-chambers could be inflated while other sub-chambers could remain non-inflated. The controller in the personal aural device would determine which chambers and sub-chambers would be inflated and which would remain non-inflated based on various factors including, without limitation, a listener controlled preference, the activity of the listener, and the detection of various forces. With such an approach, more chambers and sub-chambers could be inflated during more vigorous activity to improve retention. Likewise, fewer chambers and sub-chambers could be inflated during more passive activity to improve listener comfort.

Having described various systems and techniques related to an eartip with one or more inflatable chambers, a method for conforming an eartip to a listener's ear is now described. By implementing the described functionality, an eartip with inflatable chambers may improve the ability of individuals to listen to audio with higher audio quality, reduced discomfort, and reduced likelihood of dislodging the eartip while performing various activities.

Figure 6:
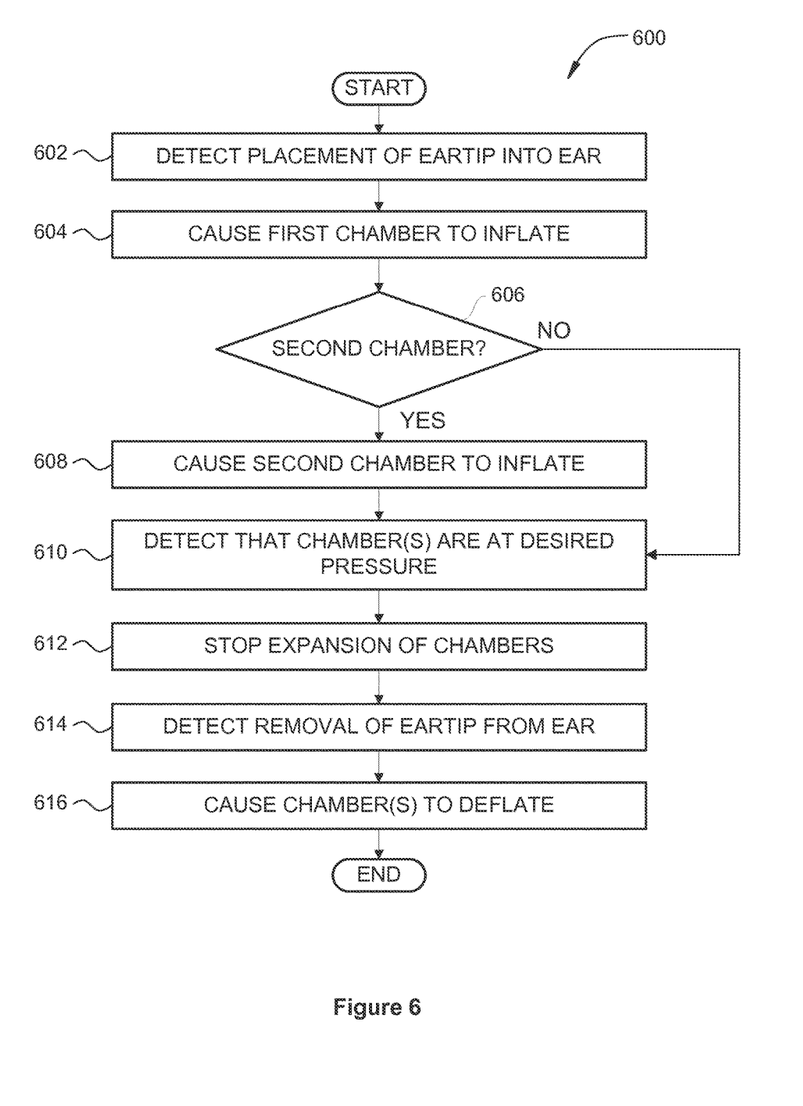
FIG. 6 is a flow diagram of method steps for fitting an eartip system into the ear of a listener, according to various embodiments.

FIG. 6 is a flow diagram of method steps for fitting an eartip system into the ear of a listener, according to various embodiments. Although the method steps are described in conjunction with the systems of FIGS. 1-5B, persons skilled in the art will understand that any system configured to perform the method steps, in any order, is within the scope of the present invention.

As shown, a method 600 begins at step 602, where a controller 170 associated with an inflatable eartip system 150 detects placement of an eartip into an ear of the listener. The controller 170 detects placement of the eartip into an ear by receiving one or more signals from an insertion sensor 160. The received signals indicate any one or more associated conditions, including, without limitation, a change in capacitance resulting from contact of the eartip with skin, a change in light condition associated with inserting the eartip, a closure of a switch when the eartip is inserted, a change in distance from the eartip to the skin, and an orientation of the eartip.

At step 604, controller 170 transmits a signal to a chamber inflator 180 to cause a first chamber to inflate. The chamber inflator 170 could inflate the chamber via any technically feasible technique, including, without limitation, pneumatic or hydraulic pumping, electrostatic flocking, magnetostriction, electrostriction of dielectrics, or a reversible chemical reaction.

At step 606, controller 170 determines whether to inflate a second chamber. If a second chamber should be inflated, then the method 600 proceeds to step 608, where controller 170 transmits a signal to a chamber inflator 180 to cause a second chamber to inflate. In various embodiments, the first signal to inflate the first chamber and the second signal to inflate the second chamber may be a single signal or separate signal. Chamber inflator 180 may inflate both chambers via the same technique. Alternatively, chamber inflator 180 may inflate the first chambers via one technique and the second chamber via a different technique.

At step 610, controller 170 detects that one or both chambers are at a desired pressure by receiving a signal from an inflation sensor 190. The signal received from inflation sensor indicates one or more associated conditions, including, without limitation, a pressure level within a chamber, a change in operating condition of chamber inflator 180, and governor or limiter associated with chamber inflator 180.

At step 612, controller 170 transmits a signal to a chamber inflator 180 to cause a first chamber to stop inflating one or more chambers. At step 614, detects removal of the eartip from the ear by receiving one or more signals from insertion sensor 160. The received signals indicate any one or more associated conditions, including, without limitation, a change in capacitance resulting from absence of contact of the eartip with skin, a change in light condition associated with removing the eartip, an open of a switch when the eartip is inserted, a change in distance from the eartip to the skin, and an orientation of the eartip. At step 616, controller 170 transmits a signal to chamber inflator 180 to cause a one or more chamber to deflate. The method 600 then proceeds to step 602, described above. In various embodiments, the steps of method 600 may be performed in a continuous loop until certain events occur, such as powering down inflatable eartip system 150.

Returning now to step 606, if controller 170 determines that a second chamber should not be inflated, then the method 600 proceeds to step 610, described above.

In sum, earphones are equipped with eartips that include one or more inflatable chambers that, when inflated, provide a custom fit that conforms to the listener's ears. In a first version, each of the eartips is equipped with a single chamber that inflates within the listener's ear canals. The inflated chamber provides a good acoustic seal to reduce loss of audio signal and provides resistance against dislodging when the listener is engaged in light activities. In a second version, each of the eartips is equipped with two chambers: one that inflates within the listener's ear canals for a good acoustic seal and one that inflates in the concha of the outer portion of the ear for greater retention relative to the first version. The chamber in the outer portion of the ear provides stronger resistance against falling out when the listener is engaged in more rigorous activities. In a third version, each of the eartips is equipped with a single chamber that inflates within the concha of the outer portion of the ear for greater retention relative to the first version. The chamber in the outer portion of the ear provides stronger resistance against falling out when the listener is engaged in more rigorous activities. Because there is no chamber within the ear canal, the listener is also able to hear more audio from the environment, such as voices or other sounds, relative to the first version.

At least one advantage of the approach described herein is that eartips in a set of earphones automatically inflate to provide an optimal fit for any listener's ears. As a result, the quality of the listener's audio experience is improved, and the potential for the eartips to cause discomfort or to fall out of the listener's ears is reduced.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, enable the implementation of the functions/acts specified in the flowchart and/or block diagram block or blocks. Such processors may be, without limitation, general purpose processors, special-purpose processors, application-specific processors, or field-programmable The flowchart and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the preceding is directed to embodiments of the present disclosure, other and further embodiments of the disclosure may be devised without departing from the basic scope thereof, and the scope thereof is determined by the claims that follow.

What is claimed is:

1. A personal aural device, comprising:
  an expandable eartip having a contracted state and an expanded state, the expandable eartip comprising:
    an insertion sensor configured to receive an indication that the eartip has been placed in an ear of a user, and
    a controller configured to, in response to the eartip being placed in the ear of the user:

actuate a first device to inflate a first chamber to a first inflation pressure to conform to a first portion of the ear that comprises a region of an ear canal, and actuate at least one of the first device and a second device to inflate a second chamber to a second inflation pressure that is different from the first inflation pressure to conform to a second portion of the ear that comprises a region of a concha.

2. The personal aural device of claim 1, wherein receiving an indication that the eartip has been placed in the ear comprises receiving a signal that indicates a change in light level.

3. The personal aural device of claim 1, wherein receiving an indication that the eartip has been placed in the ear comprises receiving a signal that indicates the eartip is horizontally oriented.

4. The personal aural device of claim 1, wherein receiving an indication that the eartip has been placed in the ear comprises determining that an audio signal is being received by the personal aural device.

5. The personal aural device of claim 1, wherein receiving an indication that the eartip has been placed in the ear comprises receiving a signal that indicates a change in capacitance consistent with the eartip being in contact with human skin.

6. The personal aural device of claim 1, wherein actuating the first device comprises actuating a pump to introduce compressed air into the first chamber.

7. The personal aural device of claim 1, wherein actuating the first device comprises transmitting an electrical charge to the eartip to orient fibers associated with the first chamber.

8. The personal aural device of claim 1, further comprising an inflation sensor configured to transmit a signal to the controller that indicates an inflation level of the first chamber, and wherein the controller is further configured to determine that the first chamber has been inflated to a desired level.

9. The personal aural device of claim 8, wherein determining that the first chamber is inflated to a desired level comprises detecting a change in at least one operating characteristic of the first device.

10. The personal aural device of claim 8, wherein determining that the first chamber is inflated to a desired level comprises receiving a signal indicating that the first chamber has achieved a threshold pressure.

11. A non-transitory computer-readable storage medium including instructions that, when executed by a processor, cause the processor to adjust an eartip associated with a personal aural device, by performing the steps of:

receiving an indication that the eartip has been placed in an ear of a user; and in response to the eartip being placed in the ear of the user:
actuating a first device to inflate a first chamber to a first inflation pressure to conform to a first portion of the ear, and
actuating at least one of the first device and a second device to inflate a second chamber to a second inflation pressure that is greater than the first inflation pressure to conform to a second portion of the ear.

12. The non-transitory computer-readable storage medium of claim 11, wherein the first portion of the ear comprises a region of an ear canal.

13. The non-transitory computer-readable storage medium of claim 11, wherein the second portion of the ear comprises a region of a concha.

14. The non-transitory computer-readable storage medium of claim 11, wherein the first portion of the ear comprises a region of an ear canal, and the second portion of the ear comprises a region of a concha.

15. A method for adjusting an eartip associated with a personal aural device, the method comprising:

receiving an indication that the eartip has been placed in an ear of a user, wherein the indication is based on determining that a first light level detected by a first portion of the eartip that is placed inside the ear is less than a second light level detected by a second portion of the eartip that remains outside of the ear; and actuating a first device, in response to the eartip being placed in the ear of the user, to inflate a first chamber to conform to a first portion of the ear.

16. The method of claim 15, wherein the first portion of the ear comprises a region of an ear canal.

17. The method of claim 15, wherein the first portion of the ear comprises a region of a concha.

18. The method of claim 15, further comprising, in response to receiving the indication that the eartip has been placed in the ear of the user, actuating a second device to inflate a second chamber to conform to a second portion of the ear.

19. The method of claim 18, wherein the first portion of the ear comprises a region of an ear canal, and the second portion of the ear comprises a region of the concha.

20. The method of claim 15, wherein both the first light level and the second light level are detected at a first time.

* * * * *